March 31, 1959 E. S. BOERNER Plant Pat. 1,823
CHRYSANTHEMUM PLANT
Filed Aug. 21, 1958
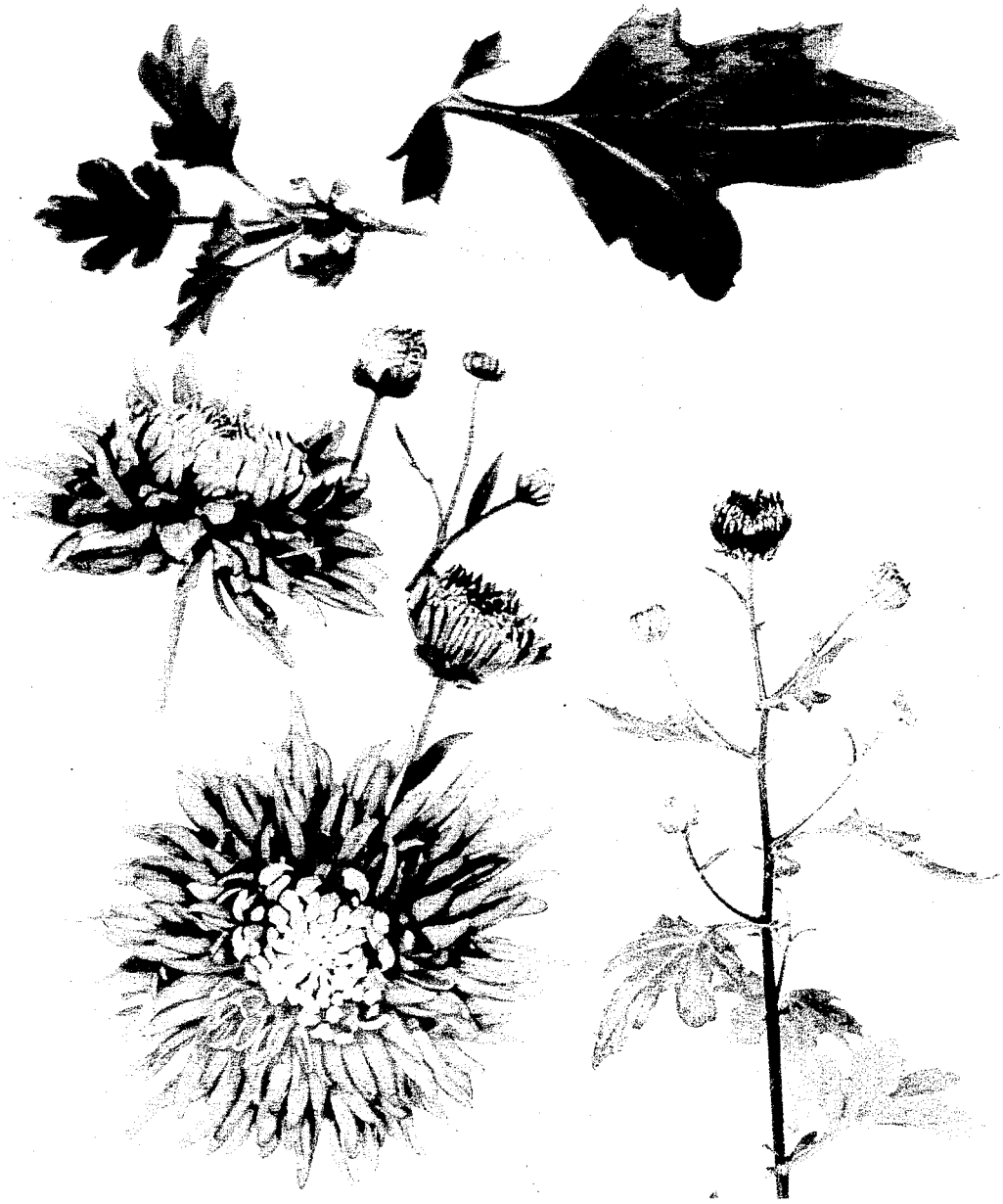
Inventor.
E. S. Boerner
By: Robb & Robb
Attorneys.

United States Patent Office

Plant Pat. 1,823
Patented Mar. 31, 1959

1,823

CHRYSANTHEMUM PLANT

Eugene S. Boerner, Newark, N.Y., assignor to Jackson & Perkins Company, Newark, N.Y., a corporation of New York Application August 21, 1958, Serial No. 756,494

1 Claim. (Cl. 47—60)

The present invention relates to a new and distinct variety of chrysanthemum plant of the decorative class, with raised center, which was originated by me by crossing an unnamed and unpatented seedling of "Chippewa" (unpatented) × "Tanager" (Plant Patent No. 1,129) with the variety "Martin" (Plant Patent No. 1,466).

The primary objective of this breeding was to produce a new chrysanthemum variety having a bright red flower color, combined with the plant vigor that is typical of both the "Chippewa" and "Tanager" varieties. This objective was fully achieved, along with other improvements, as evidenced by the following characteristics which are outstanding in the new variety and which distinguish it from its parents as well as from all other varieties of which I am aware:

(1) A vigorous habit of plant growth;

(2) A decorative flower form, with raised center;

(3) A distinctive Carmine general color tonality of the flowers; and (4) Long-lasting flower habit.

Asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black-and-white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, in the late morning near mid-October:

Parentage: An unnamed seedling of "Chippewa" × "Tanager" × "Martin."

Classification: Decorative, with raised center.

Growth: Medium height; clean; upright.

Cold resistance: Plants winter hardy in northern New York—flowers show only slight frost injury.

Blooming period: In the Newark, New York climatic area, average date of start of bloom is early October, with blooms continuing to heavy freezing.

*Flower*

Bud:

*Color.*—When sepals first divided—Scarlet Red, Plate 1. When petals begin to unfurl—Spectrum Red, Plate 1, lightly overcast with Carmine, Plate 1. When half blown: inside of petals—Carmine, Plate 1, lightly overcast with Oxblood Red, Plate 1; outside of petals—Spectrum Red, Plate 1, lightly overcast with Orange Buff, Plate 3.

*Peduncle.* — Color — Malachite Green, Plate 32. Strength—strong; erect.

Bloom:

*Size.*—5 inches.

*Stem.*—Stiff; normal.

*Form.*—Decorative.

*Petalage.*—Very double.

*Color.*—Center of flower (unfurled center)—Pale Orange-Yellow, Plate 3, lightly overcast with Scarlet Red, Plate 1. Outer petals—Nopal Red, Plate 1. Base of petals—Chalcedony Yellow, Plate 17. Inside of petals—Carmine, Plate 1. Reverse of petals—Pale Yellow-Orange, Plate 3, lightly overcast with Carmine, Plate 1.

*Petals.*—Texture—medium. Form—double.

*Fragrance.*—Characteristic chrysanthemum.

*Plant*

Form: Upright and full.

Growth: Bushy and vigorous.

Foliage:

*Size.*—Medium.

*Quantity.*—Normal.

*Color.* — Upper side — Varley's Green, Plate 18. Under side—Cress Green, Plate 31.

*Texture.*—Leathery; glossy.

I claim:

A new and distinct variety of chrysanthemum plant of the decorative class, with raised center, substantially as herein shown and described, characterized particularly as to novelty by the unique combination of a vigorous habit of plant growth, a distinctive Carmine general color tonality of the flowers, and a long-lasting flower habit.

No references cited.